(12) United States Patent
Park et al.

(10) Patent No.: US 10,449,068 B2
(45) Date of Patent: *Oct. 22, 2019

(54) METHOD FOR MANUFACTURING STENT

(71) Applicant: M.I.TECH CO., LTD., Pyeongtaek-si, Gyeonggi-do (KR)

(72) Inventors: Hun Kuk Park, Pyeongtaek-si (KR); Jong Pil Moon, Gunpo-si (KR); Bong Seok Jang, Osan-si (KR); Ho Yun, Asan-si (KR)

(73) Assignee: M.I.TECH CO., LTD., Pyeongtaek-si (KR)

( * ) Notice: Subject to any disclaimer, the term of this patent is extended or adjusted under 35 U.S.C. 154(b) by 189 days.

This patent is subject to a terminal disclaimer.

(21) Appl. No.: 15/561,754

(22) PCT Filed: May 12, 2015

(86) PCT No.: PCT/KR2015/004716
§ 371 (c)(1),
(2) Date: Sep. 26, 2017

(87) PCT Pub. No.: WO2016/167399
PCT Pub. Date: Oct. 20, 2016

(65) Prior Publication Data
US 2018/0078393 A1    Mar. 22, 2018

(30) Foreign Application Priority Data

Apr. 15, 2015 (KR) .................. 10-2015-0052979

(51) Int. Cl.
*A61F 2/90* (2013.01)
*A61F 2/86* (2013.01)
(Continued)

(52) U.S. Cl.
CPC .................. *A61F 2/90* (2013.01); *A61F 2/86* (2013.01); *A61F 2/852* (2013.01);
(Continued)

(58) Field of Classification Search
CPC .... A61F 2/86; A61F 2/90; A61F 2/851; A61F 2/852; A61F 2250/0063; A61F 2230/0054;
(Continued)

(56) References Cited

U.S. PATENT DOCUMENTS

2002/0147489 A1* 10/2002 Hong .................. A61F 2/90
623/1.2
2005/0209708 A1* 9/2005 Hong .................. A61F 2/90
623/1.15
(Continued)

FOREIGN PATENT DOCUMENTS

KR     2002-0078129 A     10/2002
KR     10-2013-0106115 A   9/2013

OTHER PUBLICATIONS

European Office Action dated Oct. 9, 2018, issued to European Application No. 15889279.4.

*Primary Examiner* — Shaun R Hurley
*Assistant Examiner* — Bao-Thieu L Nguyen
(74) *Attorney, Agent, or Firm* — Stein IP, LLC

(57) ABSTRACT

The present invention relates to a method for manufacturing a stent, the method using a jig in which detachable protruding pins are installed at all respective location points at which circumference division lines and length division lines intersect each other, the method forming cells through intersection of wire by setting any one of the location points as a start point and repeatedly bending and moving the wire from the start point upward and downward to pass over the protruding pins located in diagonal directions, wherein a first stent woven such that intersection portions formed through the intersection of a wire are spaced apart from each other in a diagonal direction and arranged one for each length division line and a second stent woven to maintain the structural stability of the first stent and to prevent the first stent from being twisted can be provided as a single stent.

10 Claims, 17 Drawing Sheets

(51) Int. Cl.
*A61F 2/852* (2013.01)
*A61F 2/915* (2013.01)

(52) U.S. Cl.
CPC ............... *A61F 2002/9155* (2013.01); *A61F 2002/91508* (2013.01); *A61F 2002/91516* (2013.01); *A61F 2002/91525* (2013.01); *A61F 2210/0076* (2013.01); *A61F 2230/0054* (2013.01); *A61F 2240/001* (2013.01); *A61F 2250/0063* (2013.01)

(58) Field of Classification Search
CPC .... A61F 2002/9155; A61F 2002/91525; A61F 2002/91516; A61F 2210/0076; A61F 2002/91508; A61F 2240/001
See application file for complete search history.

(56) References Cited

U.S. PATENT DOCUMENTS

| | | | |
|---|---|---|---|
| 2007/0118206 A1* | 5/2007 | Colgan | A61F 2/90 623/1.11 |
| 2007/0173927 A1* | 7/2007 | Shin | A61F 2/90 623/1.18 |
| 2008/0167709 A1* | 7/2008 | An | A61F 2/90 623/1.22 |
| 2009/0198315 A1* | 8/2009 | Boudjemline | A61F 2/2418 623/1.2 |
| 2010/0161034 A1* | 6/2010 | Leanna | A61F 2/90 623/1.16 |
| 2012/0191178 A1* | 7/2012 | Laduca | A61F 2/90 623/1.16 |
| 2012/0303132 A1* | 11/2012 | Kim | A61F 2/07 623/23.7 |
| 2013/0282105 A1* | 10/2013 | Shin | A61F 2/90 623/1.15 |
| 2014/0343683 A1* | 11/2014 | Jeon | A61F 2/04 623/23.7 |
| 2015/0025618 A1* | 1/2015 | Kim | A61F 2/848 623/1.15 |
| 2015/0342760 A1* | 12/2015 | Christakis | A61F 2/90 623/1.2 |
| 2016/0106559 A1* | 4/2016 | Shin | A61F 2/90 623/1.15 |
| 2016/0213498 A1* | 7/2016 | Wang | A61F 2/90 |
| 2017/0014133 A1* | 1/2017 | Han | A61F 2/90 |
| 2017/0119556 A1* | 5/2017 | Holly | A61F 2/82 |
| 2017/0143467 A1* | 5/2017 | Myung | A61F 2/04 |
| 2017/0189210 A1* | 7/2017 | Kim | A61F 2/88 |
| 2018/0185181 A1* | 7/2018 | Fredrickson | A61L 31/06 |
| 2018/0235752 A1* | 8/2018 | Wen | A61F 2/186 |
| 2018/0263626 A1* | 9/2018 | Han | A61F 2/90 |
| 2019/0029851 A1* | 1/2019 | Brady | A61F 2/844 |
| 2019/0046341 A1* | 2/2019 | Folan | A61F 2/90 |
| 2019/0053887 A1* | 2/2019 | Xiao | A61F 2/82 |
| 2019/0053926 A1* | 2/2019 | Shin | A61F 2/90 |
| 2019/0070027 A1* | 3/2019 | Wang | A61F 2/07 |

\* cited by examiner

METHOD FOR MANUFACTURING STENT

CROSS-REFERENCE TO RELATED APPLICATIONS

This application is a national stage of International Application No. PCT/KR2015/004716 filed May 12, 2015, which claims the benefit of Korean Application No. 10-2015-0052979, filed Apr. 15, 2015, in the Korean Intellectual Property Office, the disclosure of which are incorporated herein in their entireties by reference.

TECHNICAL FIELD

The present invention relates to a method for manufacturing a stent.

BACKGROUND ART

Stents manufactured for the purpose of preventing the additional progress of stenosed regions and facilitating the flow of materials within the human body through the extension of the diameters of various types of organs in the human body are each provided with specific characteristics by weaving wire, made of shape memory alloy or the like, to intersect itself according to a predetermined method.

Stents should be formed to be suitable for their purposes according to the sizes and characteristics of various types of organs and lumens and environments where the stents will be placed. For this purpose, methods for manufacturing a stent through the intersection of wire can propose various cell shapes and woven structures.

In particular, common methods for manufacturing a stent generally adopt a wire intersection method designed to perform weaving so that predetermined patterns are formed in the lengthwise or circumferential direction of a stent. For a prior art document regarding a conventional technology configured to form predetermined intersection or ring portions in the lengthwise direction as described above, there is a Korean Patent No. 10-0457629 entitled "Method for Manufacturing Variable State Maintaining Extension Device by Using Shape Memory Alloy and Extension Device Manufactured Using the Same" (hereinafter referred to as the "conventional technology").

In the case of the above conventional technology, a stent is manufactured by weaving wire according to a predetermined method, with the result that there is manufactured a stent, in which portions in each of which a structure configured such that wire sections intersect each other in the lengthwise direction are disposed and portions in each of which a ring structure configured such that wire sections form a predetermined space in the lengthwise direction are alternately formed.

However, a stent manufactured via the conventional technology cannot provide sufficient stress and resisting force in the case where force is applied from both ends of the stent to the center of the stent due to external force imposed on the placed stent or due to the movement of a region where the stent has been placed after the stent has been placed in order to restore a stenosed region. Accordingly, the stent has the problem of being bent or dislodged from the location where the stent has been placed.

Furthermore, a stent manufactured via the conventional technology is problematic in that metallic fatigue imposed on the wire of the stent increases due to contact between wire structures and due to the twisting of wire structures attributable to the bending of the stent, thus resulting in a reduction in the life span of the wire.

DISCLOSURE

Technical Problem

The present invention has been conceived to overcome the above-described problems, and an object of the present invention is to provide technology capable of manufacturing a stent which can overcome external force continuously applied to both ends of the stent due to the movement of a region where the stent has been placed and which has sufficient structural flexibility.

Technical Solution

In order to accomplish the above object, the present invention provides a method for manufacturing a stent, the method using a jig in which detachable protruding pins are installed at all respective location points at which circumference division lines and length division lines, set by equally dividing the circumference W and length L of a cylinder having a diameter R and the length L identical to those of a stent to be manufactured, intersect each other, the method forming cells through the intersection of wire by setting any one reference point of the location points as a start point and repeatedly bending and moving the wire from the start point upward and downward to pass over the protruding pins located in diagonal directions, the method including: step A of forming part of a first body by moving a first wire in a zigzag form from a first start point at one end of the jig to a first point at the other end of the jig; step B of forming a lower first head by repeating a pattern of bending the first wire in a zigzag form from the first point to a first change point at the other end of the jig; step C of forming part of the first body by bending and moving the first wire in a zigzag form from the first change point to a second point at the one end of the jig; and step D of forming an upper first head by repeating a pattern of bending the first wire in a zigzag form from the second point to the first start point; wherein step A includes: step A-1 of moving the first wire from the first start point along an upward diagonal line by l (the distance of a diagonal line extending by one interval between the length division lines with respect to one interval between the circumference division lines); and step A-2 of spacing a corresponding location point from a portion formed at step A-1 by moving the first wire from the end point of step A-1 along a downward diagonal line by 2l; wherein step C includes: step C-1 of repeating a zigzag bent pattern formed by moving the first wire from the first change point along a downward diagonal line by l and then moving the first wire from a corresponding location point along an upward diagonal line by l; and step C-2 of spacing a corresponding location point from a portion formed at step C-1 by moving the first wire from the end point of step C-1 along an upward diagonal line by 2l; wherein step A includes alternately repeating the patterns of step A-1 and step A-2; and wherein step C includes alternately repeating the patterns of step C-1 and step C-2.

In this case, the number of circumference division lines may be 6+4x (x: 0 or a natural number), and the number of length division lines may be 11+5y (y: 0 or a natural number). Additionally, the first point may correspond to an end point which is one of the plurality of end points of step A-1 formed during the repetition of step A-1 and step A-2 and which is also located on a length division line symmetrical to a length division line where the first start point is located; and the second point may correspond to an end point which is one of the plurality of end points of step C-1 formed during the repetition of step C-1 and step C-2 and which is also located on the same length division line as the first start point.

Furthermore, step B may include: step B-1 of moving the first wire from the first point along a downward diagonal line by 2l; step B-2 of repeating a zigzag bent pattern formed by moving the first wire from a location point, reached at step B-1, along an upward diagonal line by l and then moving the first wire from a corresponding location point along a downward diagonal line by l; and step B-3 of locating the first wire at the first change point by moving the first wire from a location point, reached at step B-2, along an upward diagonal line by 2l; and the location point reached at step B-2 may be located on the same circumference division line as the first point.

Furthermore, step D may include: step D-1 of moving the first wire from the second point along an upward diagonal line by 2l; step D-2 of repeating a zigzag bent pattern formed by moving the first wire from a location point, reached at step D-1, along a downward diagonal line by l and then moving the first wire from a corresponding location point along an upward diagonal line by l; and step D-3 of locating the first wire at the first start point by moving the first wire from a location point, reached at step D-2, along a downward diagonal line by 2l; and the location point reached at step D-2 may be located on the same circumference division line as the second point.

Moreover, the method may further include: step E of forming part of a second body by bending and moving a second wire in a zigzag form from a second start point at the other end of the jig to a third point at the one end of the jig; step F of forming an upper second head by repeating a pattern of bending the second wire in a zigzag form from the third point to a second change point at the one end of the jig; step G of forming part of the second body by bending and moving the second wire in a zigzag form from the second change point to a fourth point at the other end of the jig; and step H of forming a lower second head by repeating a pattern of bending the second wire in a zigzag form from the fourth point to the second start point; step E may include: step E-1 of repeating a zigzag bent pattern formed by moving the second wire from the second start point along a downward diagonal line by l and then moving the second wire from a corresponding location point along an upward diagonal line by l; and step E-2 of spacing a corresponding location point from a portion formed at step E-1 by moving the second wire from the end point of step E-1 along an upward diagonal line by 2l; step G may include: step G-1 of repeating a zigzag bent pattern formed by moving the second wire from the second change point along an upward diagonal line by l and then moving the second wire from a corresponding location point along a downward diagonal line by l; and step G-2 of spacing a corresponding location point from a portion formed at step G-1 by moving the second wire from the end point of step G-1 along a downward diagonal line by 2l; step E may include alternately repeating the patterns of step E-1 and step E-2; step G may include alternately repeating the patterns of step G-1 and step G-2; and step E-2 may include moving the second wire so that during the movement of the second wire, the second wire is located over the first wire at one of two points at which the first wire and the second wire woven on the jig intersect each other and the second wire is located beneath the first wire at the other point of the two points.

In this case, the second start point may correspond to a location which is reached by moving a corresponding circumference division line by an odd number of intervals in a circumferential direction along a length division line symmetrical to a length division line where the first start point is located.

Furthermore, the third point may correspond to an end point which is one of the plurality of end points of step E-1 formed during the repetition of step E-1 and step E-2 and which is also located on a length division line symmetrical to a length division line where the second start point is located; and the fourth point may correspond to an end point which is one of the plurality of end points of step G-1 formed during the repetition of step G-1 and step G-2 and which is also located on the same length division line as the second start point.

Step F may include: step F-1 of moving the second wire from the third point along an upward diagonal line by 2l; step F-2 of repeating a zigzag bent pattern formed by moving the second wire from a location point, reached at step B-1, along a downward diagonal line by l and then moving the second wire from a corresponding location point along an upward diagonal line by l; and step F-3 of locating the second wire at the second change point by moving the second wire from a location point, reached at step F-2, along a downward diagonal line by 2l; and the location point reached at step F-2 may be located on the same circumference division line as the third point.

Additionally, step H may include: step H-1 of moving the second wire from the fourth point along a downward diagonal line by 2l; step H-2 of repeating a zigzag bent pattern formed by moving the second wire from a location point, reached at step H-1, along an upward diagonal line by l and then moving the second wire from a corresponding location point along a downward diagonal line by l; and step H-3 of locating the second wire at the second start point by moving the second wire from a location point, reached at step H-2, along an upward diagonal line by 2l; and the location point reached at step H-2 may be located on the same circumference division line as the fourth point.

Advantageous Effects

The stent formed in a predetermined cell structure by bending and weaving wires by means of a predetermined method according to the present invention has the following effects:

First, in the overall structure of the stent formed via the first wire, the intersection portions are provided in a diagonal direction along a circumferential direction one for each length division line and form a spiral arrangement structure, thereby providing sufficient resisting force-type stress against forces applied to both ends of the stent due to the movement of a stenosed region after the stent has been placed in the stenosed region and due to external force.

Second, a spiral intersection arrangement structure is equipped and thus sufficient stress is provided against force applied to both ends of the stent, thereby preventing the stent from being bent or dislodged from a region where the stent has been placed.

Third, the stent has high-level structural flexibility, can come into tight contact with the wall of a lumen regardless of the types of lumens bent in various forms, and can push a stenosed region.

Fourth, a stent structure is additionally reinforced by moving the second wire so that the second wire is caught in a structure formed by the first wire during a process of forming an outer structure by bending and weaving the second wire outside the stent formed via the first wire according to a predetermined method, and thus the structural characteristics of the stent formed via the first wire can be improved, thereby preventing the stent wires from being twisted and also providing a stent having higher-level flexibility and durability.

MODE FOR INVENTION

Preferred embodiments of the present invention will be described in greater detail below with reference to the accompanying drawings. Well-known technical portions will be omitted or abridged for brevity of description.

1. <Description of a Method for Manufacturing a Stent>

Figure 16:
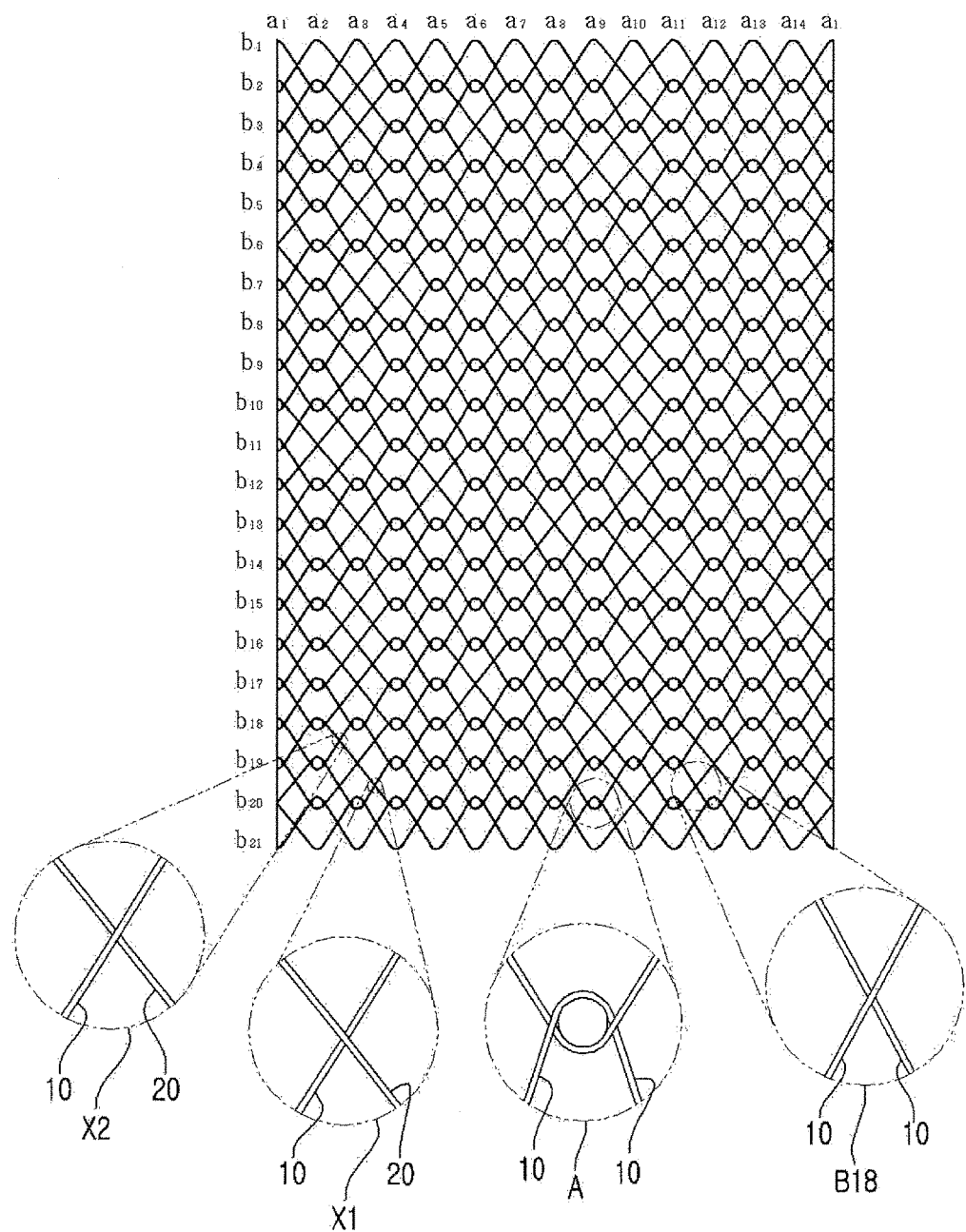
Figure 17:
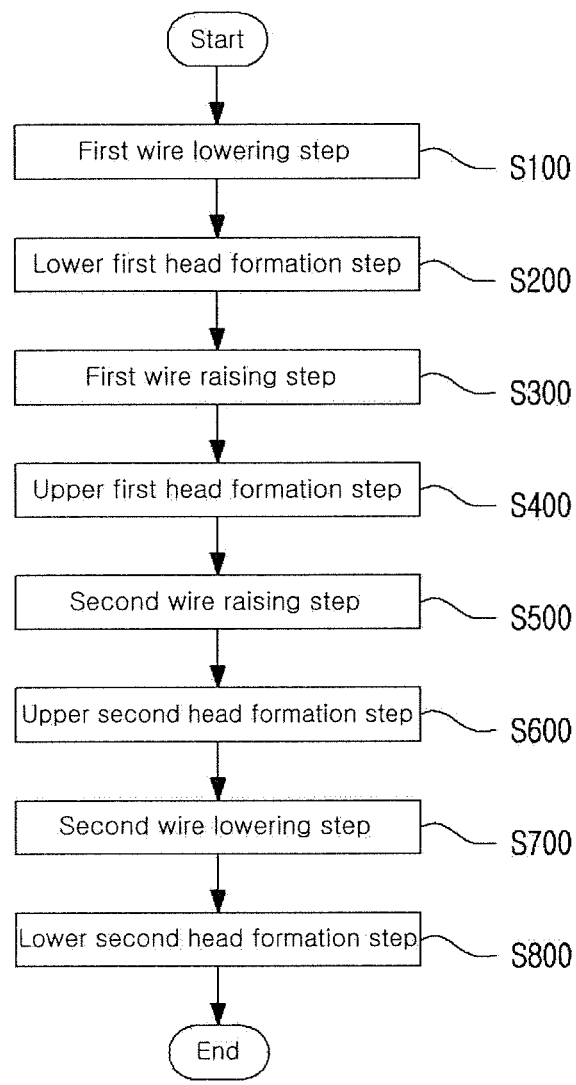
FIG. 17 is a flowchart showing a method for manufacturing a stent according to the present invention.

A process in which a method for manufacturing a stent according to the present invention is performed will be described in detail below with reference to the flowchart of FIG. 17 and the developments of FIGS. 1 to 16.

Figure 1:
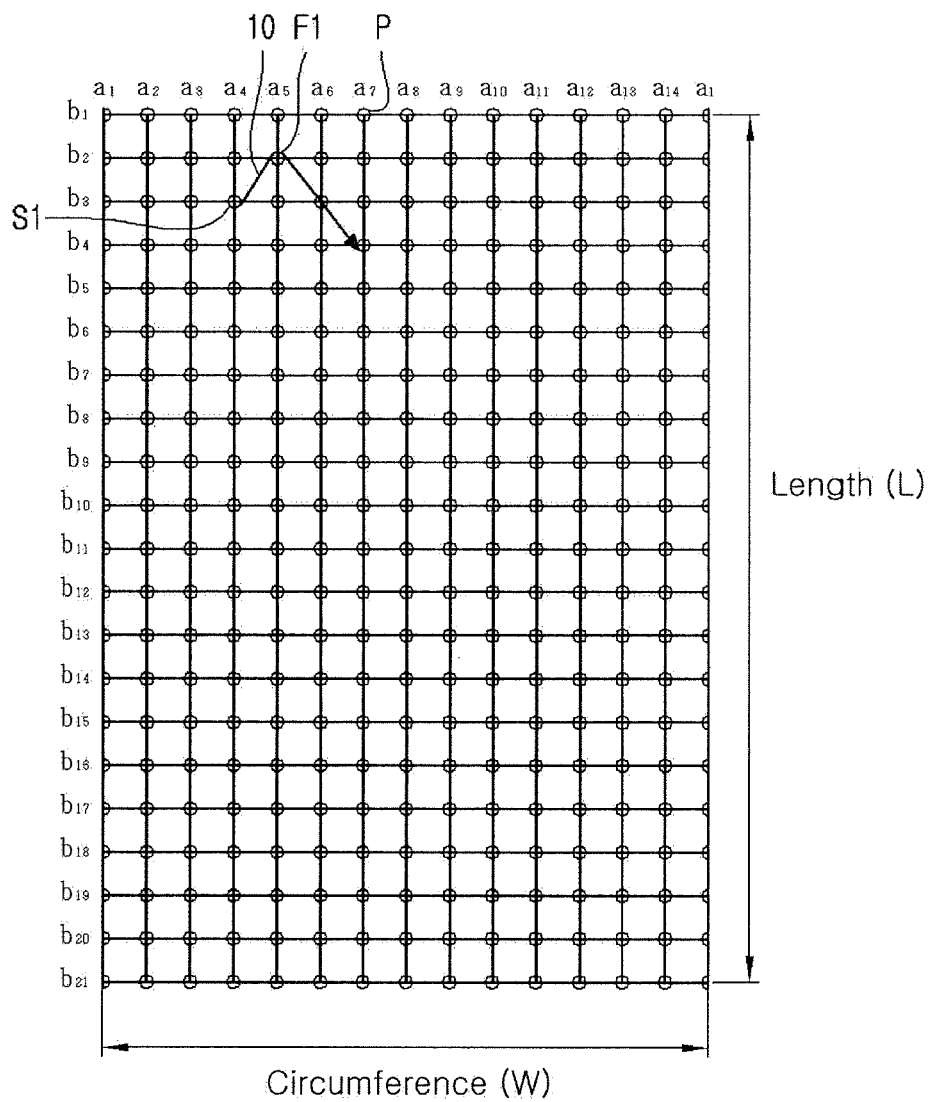
FIGS. 1 and 2 are developments illustrating a first wire lowering step according to the present invention.
Figure 2:
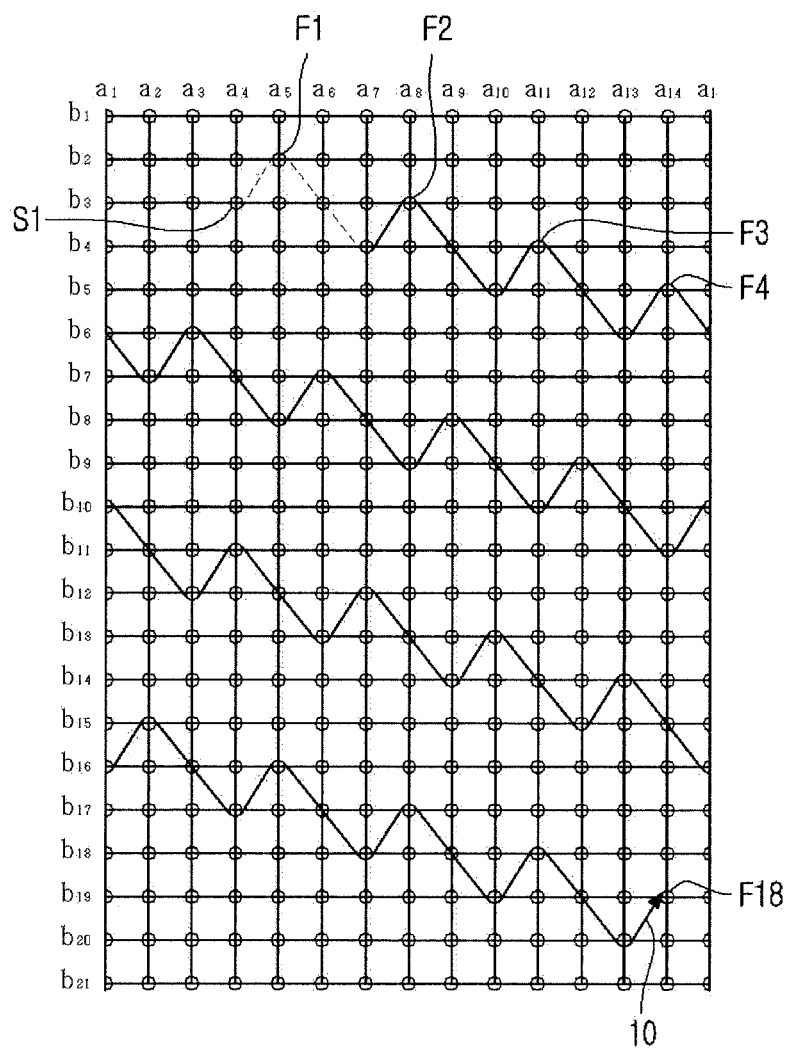
Figure 3:
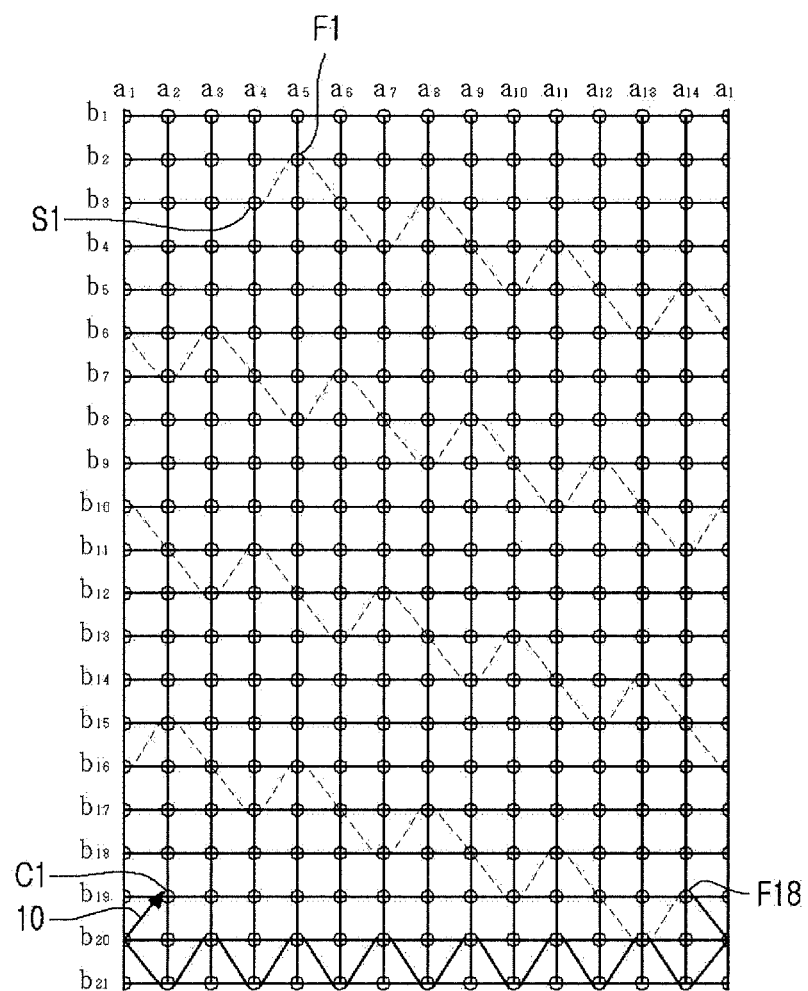
FIG. 3 is a development illustrating a lower first head formation step according to the present invention.

First, FIGS. 1 to 3 show a structure and method which are formed or performed by a first wire 10 in a method for manufacturing a stent by using a jig according to an embodiment of the present invention, and FIGS. 9 to 16 show a structure and method which are formed or performed via a second wire in order to reinforce the structure of a completed stent after the first wire 10 has been moved in the method for manufacturing a stent by using a jig according to the embodiment of the present invention.

In the drawings, the dotted lines represent the paths of moved wires, and the solid lines represent the paths of wires to be moved at corresponding steps of individual drawings. In FIGS. 9 to 16, in order to distinguish the structures formed by the first wire 10 from the structures formed by the second wire 20, the thinner solid lines are used. This is arbitrarily set for ease of description, and is unrelated to the properties and diameters of wires used in the stent which is actually manufactured according to the present invention.

In this case, in the jig, detachable protruding pins P are installed at all the location points at which circumference division lines $a_1, a_2, a_3, \ldots, a_{14}$ and length division lines $b_1, b_2, b_3, \ldots, b_{21}$, set by equally dividing the circumference W and length L of a cylinder having a diameter R and the length L identical to those of a stent to be manufactured, intersect each other. Using the jig, a stent is manufactured by setting any one of the location points as a start point and repeatedly bending and moving the wire 10 from the start point upward and downward to pass over the protruding pins P located in diagonal directions, thereby making intersections and thus forming cells.

Furthermore, the number of circumference division lines of the jig is defined as 6+4x (x: 0 or a natural number). The number of circumference division lines of the jig, which is a basis for the following description based on an embodiment of the present invention, is 14 in the case where x=2.

Moreover, the number of length division lines of the jig is defined as 11+5y (y: 0 or a natural number). The number of length division lines of the jig, which is a basis for the following description based on the embodiment of the present invention, is 21 in the case where y=2.

(1) First Wire Lowering Step <S100>

As shown in FIGS. 1 to 2, at the present step (step A), part of the first body of a stent which is manufactured according the present invention is formed by bending and moving the first wire 10 in a zigzag form from a first start point S1 ($a_4/b_3$) at one end of the jig to a first point F18 ($a_{14}/b_{19}$) at the other end of the jig.

This process includes: a movement step (step A-1) of moving the first wire 10 from the location point S1 along an upward diagonal line by (the distance of a diagonal line extending by one interval between the length division lines with respect to one interval between the circumference division lines), as shown in FIG. 1; and a first spacing step (step A-2) of spacing a corresponding location point from a portion F1 formed at the first movement step by moving the first wire 10 from the end point F1 ($a_5/b_2$) of the movement step along a downward diagonal line by 2l, as shown in FIG. 1.

The patterns of the movement step and the first spacing step are alternately repeated, and the movement step to be performed after the first spacing step starts from a location point $a_7/b_4$ reached by spacing the first wire 10 via the previously performed first spacing step. As shown in FIG. 2, the above-described patterns of the two steps are repeated, and then the first wire lowering step S100 is terminated at the end point F18 of a specific movement step.

As a result, a first point, which is the last location point of the first wire lowering step S100 and which is also the start location point of a lower first head formation step S200, corresponds to the last end point F18 of a plurality of end points F1, F2, F3, . . . , F18 formed during the process in which the movement step and the first spacing step are alternately performed. This first point F18 refers to an end point which is one of the plurality of end points F1, F2, F3, . . . , F18 formed during the process in which the movement step and the first spacing step are alternately performed and which is also located on the length division line $b_{19}$ symmetrical to the length division line $b_3$ where the first start point S1 is located.

(2) Lower Head Formation Step <S200>

As shown in FIG. 3, at the present step (step B), there is performed a process of forming a lower first head by repeating a pattern of bending the first wire 10 in a zigzag form from the first point F18, reached after the first wire 10 has formed the part of the first body of the stent while being lowered via S100 (step A), to a first change point C1 ($a_2/b_{19}$) at the other end of the jig.

In this case, the first wire 10 is moved from the first point F18 along a downward diagonal line by 2l, as shown in FIG. 3 (step B-1).

Thereafter, a zigzag bent pattern formed by moving the first wire 10 from a corresponding location point $a_2/b_{21}$ along an upward diagonal line by 1 and then moving the first wire 10 from a corresponding location point $a_3/b_{20}$ along a downward diagonal line by 1 is repeated until the first wire 10 is located on the same circumference division line $a_{14}$ as the first point F18 (step B-2).

Finally, the first wire 10 is located at the first change point C1 by moving the first wire 10 from a location point $a_{14}/b_{21}$, reached as a result of the above step, along an upward diagonal line by 2l (step B-3).

(3) First Wire Raising Step <S300>

Figure 4:
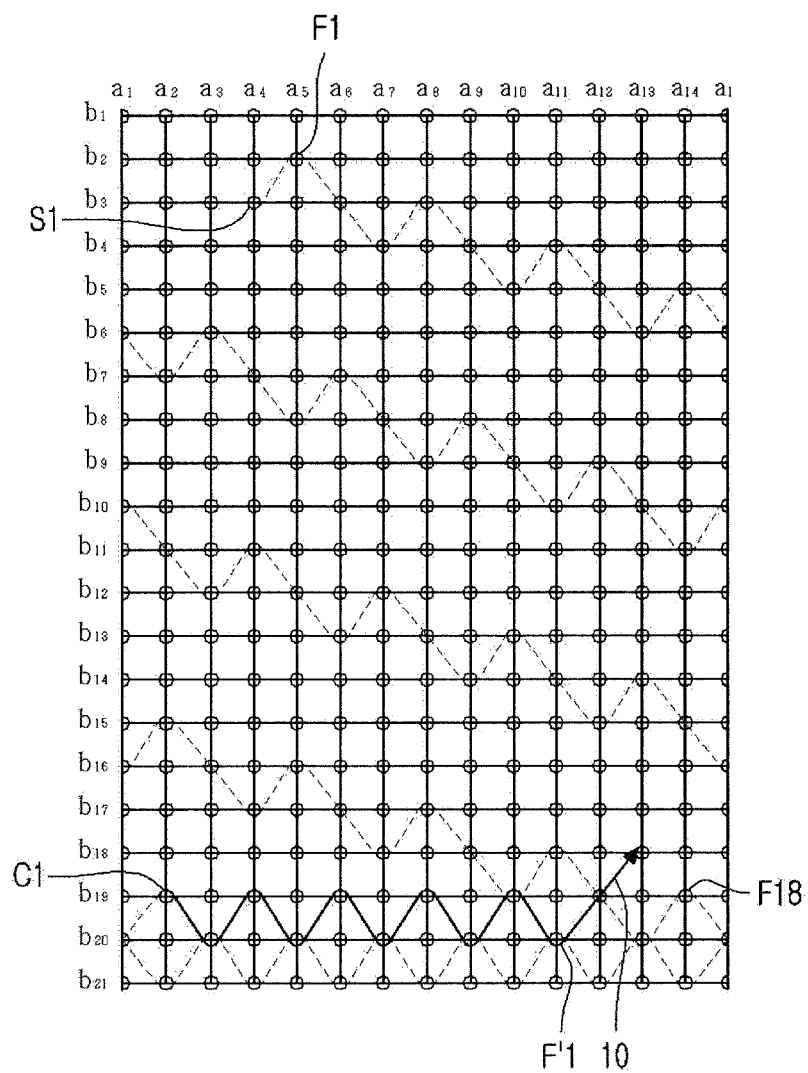
FIGS. 4 and 5 are developments illustrating a first wire raising step according to the present invention.
Figure 5:
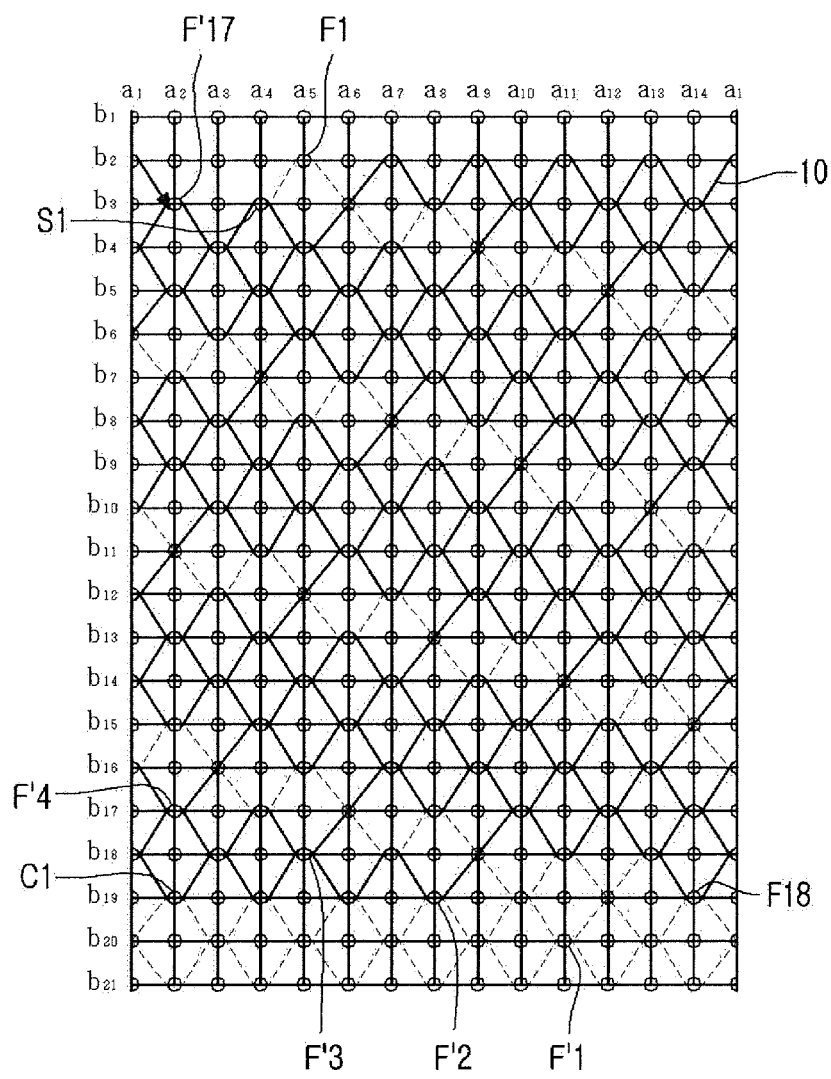

As shown in FIGS. 4 and 5, at the present step (step C), part of the first body of the stent which is manufactured according to the present invention is formed by bending and moving the first wire 10 in a zigzag form from the first change point C1 at the other end of the jig to a second point F'17 ($a_2/b_3$) at the one end of the jig.

As shown in FIG. 4, this process includes: a first zigzag movement step (step C-1) of repeating a zigzag bent pattern formed by moving the first wire 10 from the change point C1 along a downward diagonal line by 1 (the distance of a diagonal line extending by one interval between the length division lines with respect to one interval between the circumference division lines) and then moving the first wire 10 from a location point $a_3/b_{20}$ along an upward diagonal line by l; and a second spacing step (step C-2) of spacing a corresponding location point from a portion formed at the zigzag movement step by moving the first wire 10 from the end point F'1 ($a_{11}/b_{20}$) of the first zigzag movement step along an upward diagonal line by 2l.

The patterns of the first zigzag movement step and the second spacing step are alternately repeated, and the first zigzag movement step to be performed after the first second spacing step starts from a location point $a_{13}/b_{18}$ reached by moving the first wire 10 at the previously performed second spacing step. As shown in FIG. 5, the above-described patterns of the two steps are repeated, and then the first wire raising step S300 is terminated at the end point F'17 ($a_2/b_3$) of a specific first zigzag movement step.

As a result, a second point, which is the last location point of the first wire raising step S300 and which is also the start location point of an upper first head formation step S400, corresponds to the last end point F'17 of many end points F'1, F'2, F'3, . . . , F'17 formed during the process in which the first zigzag movement step and the second spacing step are alternately performed. The second point F'17 refers to an end point which is one of many end points F'1, F'2, F'3, . . . , F'17 formed during the process in which the first zigzag movement step and the second spacing step are alternately performed and which is located on the same length division line as the first start point S1.

(4) Upper First Head Formation Step <S400>

Figure 6:
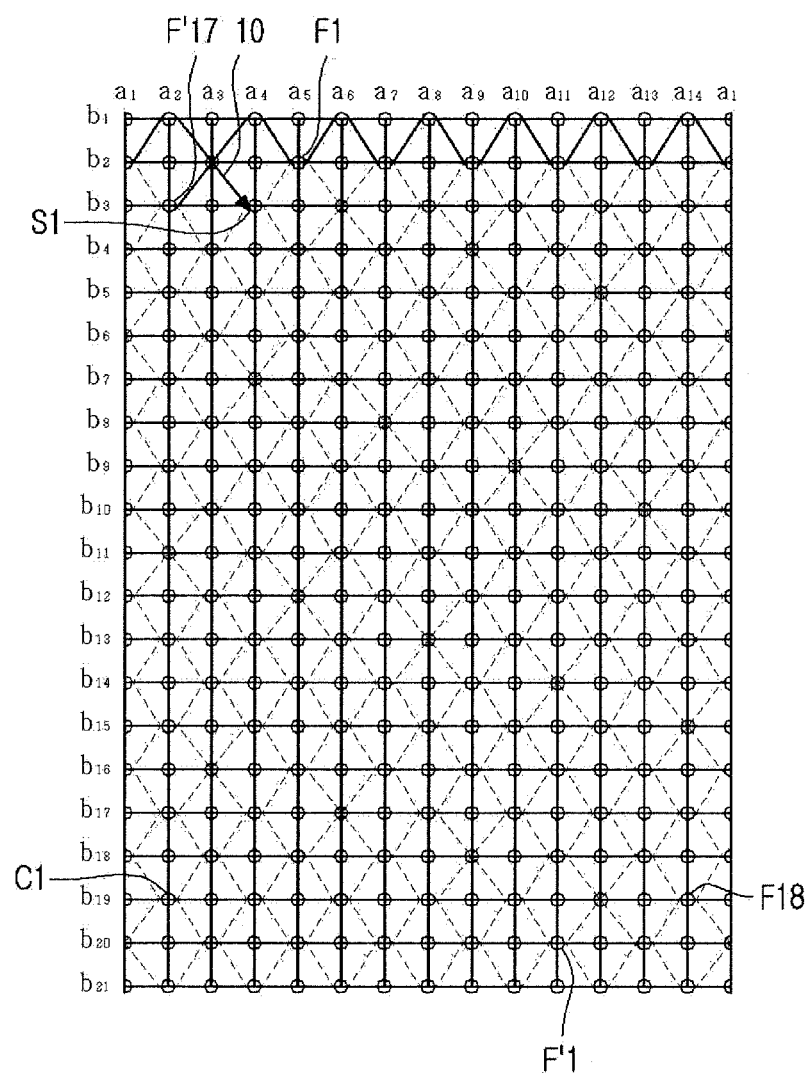
FIG. 6 is a development illustrating an upper first head formation step according to the present invention.

As shown in FIG. 6, at the present step (step D), there is performed a process of forming an upper first head by repeating a pattern of bending the first wire 10 in a zigzag form from the second point F'17, reached after the first wire has completed the intersection structure of the first wire 10 forming the part of the first body of the stent while being raised via step S300 (step C), to the first start point S1 at the one end of the jig.

In this case, the first wire 10 is moved from the second point F'17 along an upward diagonal line by 2l, as shown in FIG. 6 (step D-1).

Thereafter, a zigzag bent pattern formed by moving the first wire 10 from a corresponding location point $a_4/b_1$ along a downward diagonal line by l and then moving the first wire 10 from a corresponding location point $a_5/b_2$ along an upward diagonal line by 1 is repeated until the first wire 10 is located on the same circumference division line $a_2$ as the second point F'17 (step D-2).

Finally, the first wire 10 is located at the first start point S1 by moving the first wire 10 from a location point $a_2/b_1$, reached as a result of the above step, along an upward diagonal line by 2l (step D-3).

Figure 7:
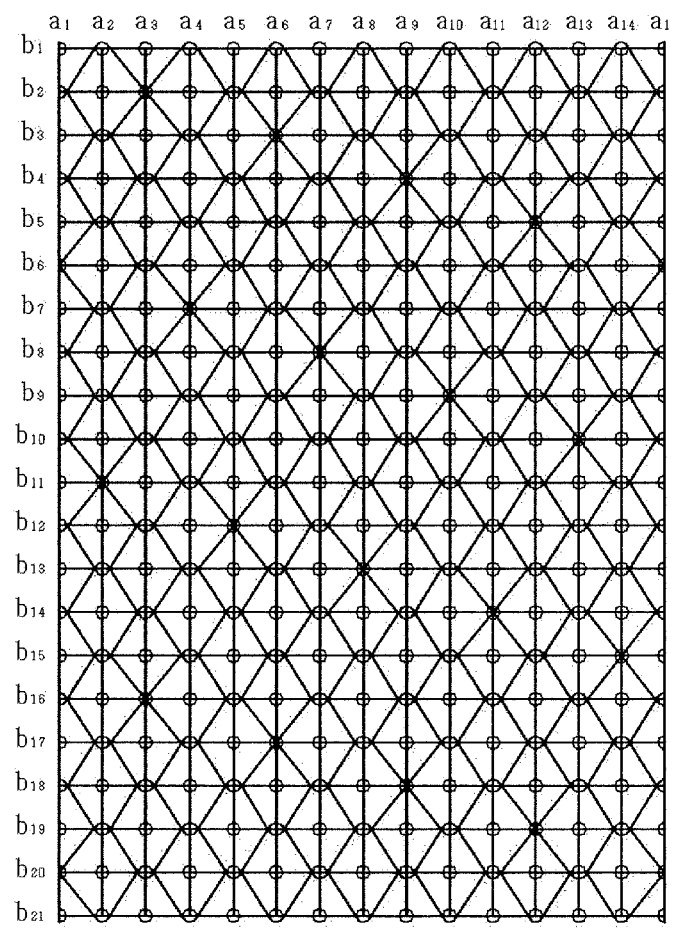
FIGS. 7 and 8 are developments showing the overall intersection and bending state of a first wire according to the present invention.
Figure 8:
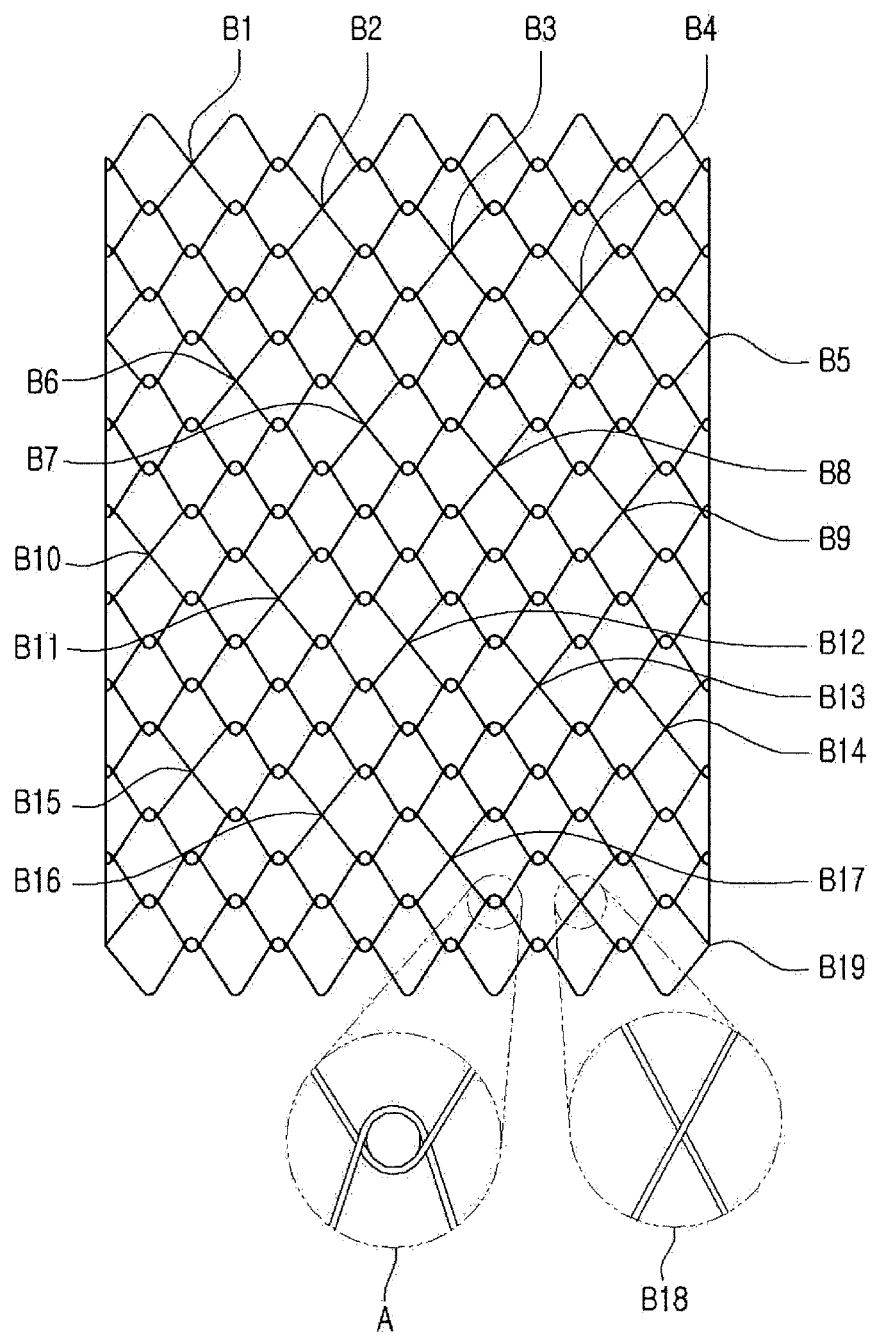

As shown in FIGS. 7 and 8, the first wire 10 returned to the first start point S1 as described above is finally connected through welding or the like, and forms the first stent having predetermined structural characteristics.

In other words, as shown in FIG. 8, in the structure of the first stent manufactured via steps S100 to S400, ring-shaped portions A, in each of which two wire sections intersect each other in the form of being hooked around each other and an empty circular space is provided at the center thereof by a corresponding protruding pin P, and intersections B, at each of which one wire section simply passes over another wire section, are formed in a predetermined arrangement. More specifically, the intersections B are formed in a diagonal direction in a spiral form one for each length division line, and the ring-shaped portions A are formed in the remaining portions.

In other words, as shown in FIGS. 7 and 8, in the first stent manufactured via steps S100 to S400, a plurality of intersections B2, B3, B4, . . . , B19 are formed from the intersection B1, formed at a specific location point $a_3/b_2$ on the second length division line $b_2$, along a diagonal line having a predetermined slope at regular intervals.

For the structural reinforcement of the first stent manufactured as described above, the designer manufactures a second stent disposed outside the first stent as a reinforcing member by additionally selecting and performing the following steps S500 to S800 via a second wire 20, and connects the first stent and the second stent to each other, thereby enabling a single stent, including the two stents having respective wire structures, to be manufactured.

(5) Second Wire Raising Step <S500>

Figure 9:
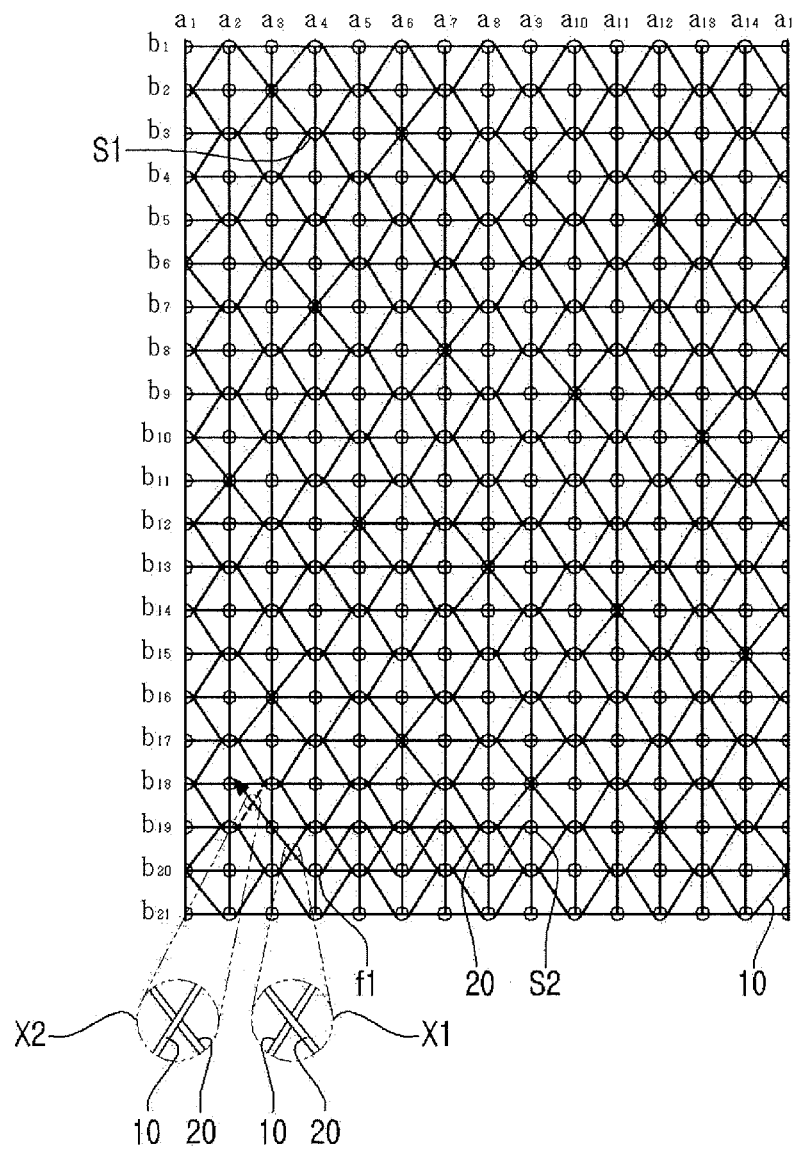
FIGS. 9 and 10 are developments illustrating a second wire raising step according to the present invention.
Figure 10:
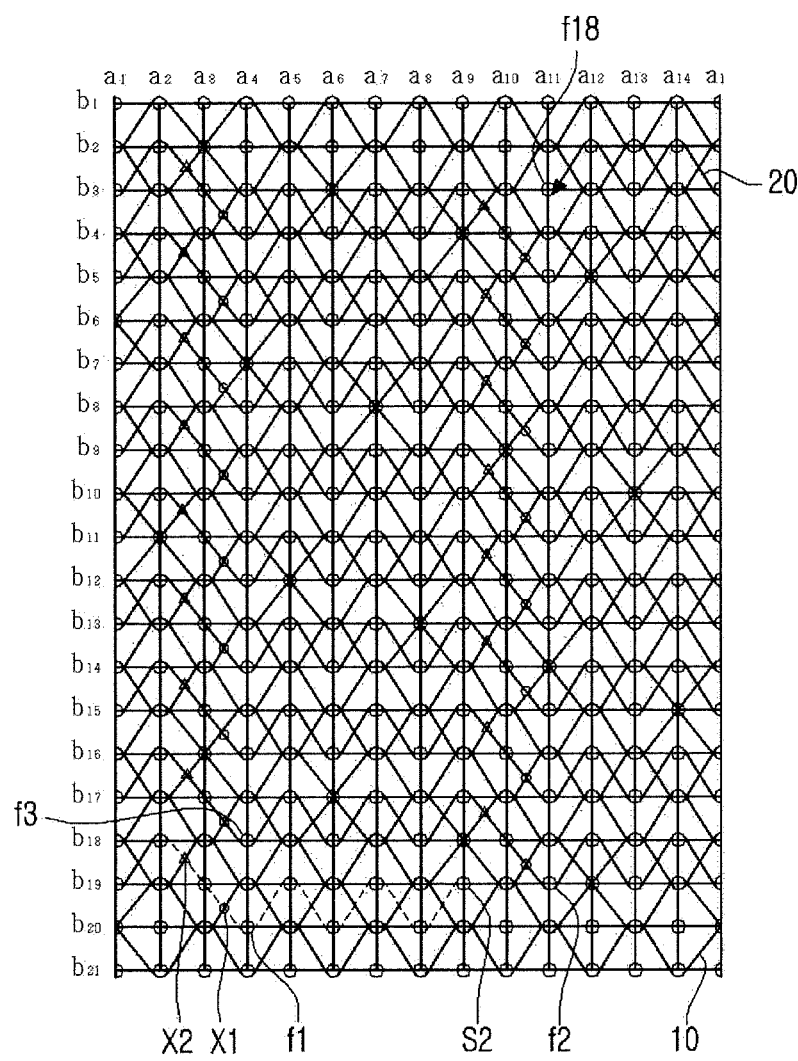

As shown in FIGS. 9 and 10, at the present step (step E), part of the second body of the stent which is manufactured according to the present invention is formed by bending and moving the second wire 20 in a zigzag form from a second start point S2 ($a_9/b_{19}$) at the other end of the jig to a third point f18 ($a_{11}/b_3$) at the one end of the jig.

It is preferred that the present step (step E) is performed on the jig, on which the first wire 10 has been manufactured, after steps S100 to S400 via the first wire 10 have been all performed.

In this case, the second start point S2 corresponds to a location reached by moving a corresponding circumference division line by an odd number of intervals in the circumferential direction along the length division line $b_{19}$ symmetrical to the length division line $b_3$ where the first start point S1 is located. More specifically, based on the length division line $b_{19}$ symmetrical to the length division line $b_3$ where the first start point S1 is located, the circumference division line where the second start point S2 is located corresponds to the circumference division line reached by moving the circumference division line $a_4$, where the first start point S1 is located, by five intervals, as shown in FIG. 9. This may be provided to start from a circumference division line reached by movement through any other odd number of intervals, such as one interval or three intervals.

Furthermore, the second start point S2 is located on the length division line $b_{19}$ on the other end side of the jig symmetrical to the length division line $b_3$ on a one end side of the jig where the first start point S1 is located. This allows the locations, at which knots are formed during a process of performing final connection after the overall movement of the wire has been completed, to be distributed between both end sides, thereby preventing imbalance in the overall volume of the stent which occurs when the knots are concentrated on one end side. Furthermore, for ease of design, it is preferred that the designer turns the jig upside down and manufactures the stent by moving the wire in the state in which the second start point is set on an upper side.

This process includes: a second zigzag movement step (step E-1) of repeating a zigzag bent pattern formed by moving the second wire 20 from the second start point S2 along a downward diagonal line by l (the distance of a diagonal line extending by one interval between the length division lines with respect to one interval between the circumference division lines) and then moving the second wire 20 from a corresponding location point $a_8/b_{20}$ along an upward diagonal line by l, as shown in FIG. 9; and a third spacing step (step E-2) of spacing a corresponding location point from a portion formed at the zigzag movement step by moving the second wire 20 from the end point f1 ($a_4/b_{20}$) of the second zigzag movement step along an upward diagonal line by 2l, as shown in FIG. 9.

The patterns of the second zigzag movement step and the third spacing step are alternately performed, and the second zigzag movement step to be performed after the first third spacing step starts from a location point $a_2/b_{18}$ reached by spacing the second wire 20 via the previously performed third spacing step. As shown in FIG. 10, the above-described patterns of the two steps are repeated, and then the second wire raising step S500 is terminated at the end point f18 of a specific third zigzag movement step.

In this case, as shown in FIG. 9, the second wire 20 moved from the end point f1 of the second zigzag movement step along the upward diagonal line by a via the third spacing step form two intersection points. At one point (an intersection point formed in a space between $a_3$ and $a_4$ and between $b_{19}$ and $b_{20}$) of the two intersection points, the second wire is located over the first wire 10 (which is indicated by a small circle in FIG. 10; X1); and at the remaining point (an intersection point formed in a space between $a_2$ and $a_3$ and between $b_{18}$ and big), the second wire 20 is located beneath the first wire 10 (which is indicated by a small triangle in FIG. 10; X2).

As shown in FIG. 10, this movement method is applied to each process of moving the second wire 20 from each of the plurality of end points f1, f2, f3, . . . , f17 of the second zigzag movement step along an upward diagonal line by 2l during the repetition of the third spacing step.

In other words, in the connection structure of the first wire 10 and the second wire 20 formed via the above process, the second wire 20 is passed beneath the first wire 10 (see X2) only in spaces between the circumference division line $a_2$ and the circumference division line $a_3$ and between the circumference division line $a_9$ and the circumference division line $a_{10}$, as shown in FIG. 10, thereby achieving a structural characteristic capable of preventing the wire structure of the first stent from being twisted.

As a result, a third point, which is the last location of the second wire raising step S500 and which is also the start location of an upper second head formation step S600, corresponds to the last end point f18 of many end point f1, f2, f3, . . . , f18 formed during the process in which the second zigzag movement step and the third spacing step are alternately performed. This third point f18 refers to an end point which is one of many end point f1, f2, f3, . . . , f18 formed during the process in which the second zigzag movement step and the third spacing step are alternately performed and which is also located on the length division line $b_3$ symmetrical to the length division line $b_{19}$ where the second start point S2 is located.

(6) Upper Second Head Formation Step <S600>

Figure 11:
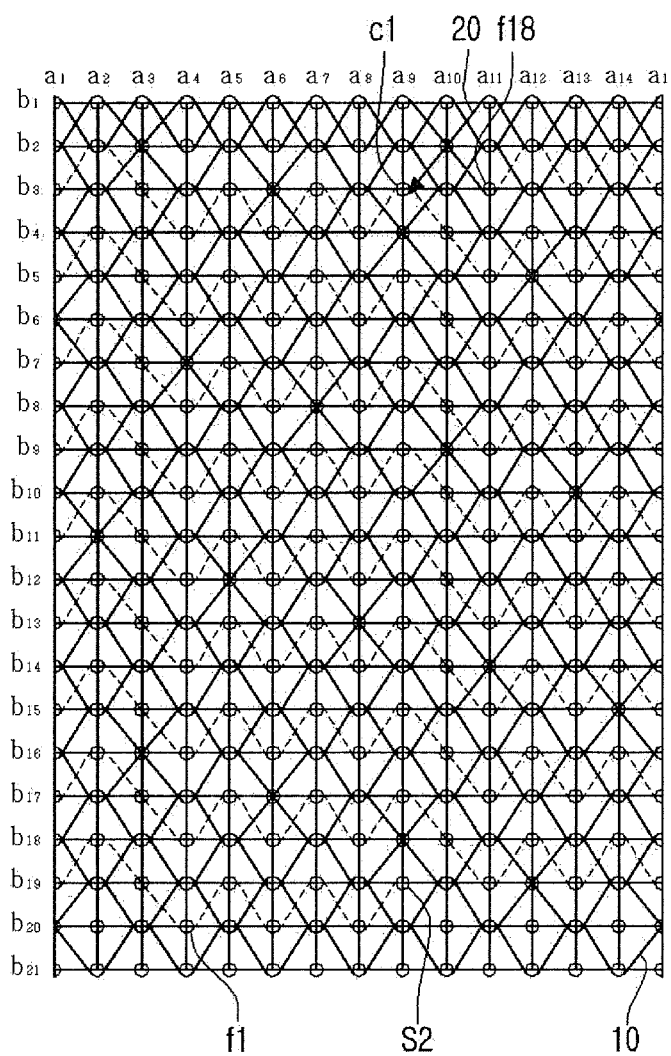
FIG. 11 is a development illustrating a lower second head formation step according to the present invention.

As shown in FIG. 11, at the present step (step F), there is performed a process of forming an upper second head by repeating a pattern of bending the second wire 20 in a zigzag form from the third point f18, reached after the second wire 20 has formed the part of the second body of the stent while being raised via step S500 (step E), to a second change point c1 ($a_9/b_3$) at the one end of the jig, thus resulting in the completion of the intersection structures of the wires 10 and 20 of the overall upper head.

In this case, as shown in FIG. 11, the second wire 20 is moved from the third point f18 along an upward diagonal line by 2l (step F-1).

Thereafter, a zigzag bent pattern formed by moving the second wire 20 from a corresponding location point $a_8/b_1$ along a downward diagonal line by l and then moving the second wire 20 from a corresponding location point $a_8/b_2$ along an upward diagonal line by £ is repeated until the second wire 20 is located on the same circumference division line $a_{11}$ as the third point f18 (step F-2).

Finally, the second wire 20 is located at the second change point c1 by moving the second wire 20 from a location point $a_{11}/b_1$, reached as a result of the above step, along a downward diagonal line by a (step F-3).

(7) Second Wire Lowering Step <S700>

Figure 12:
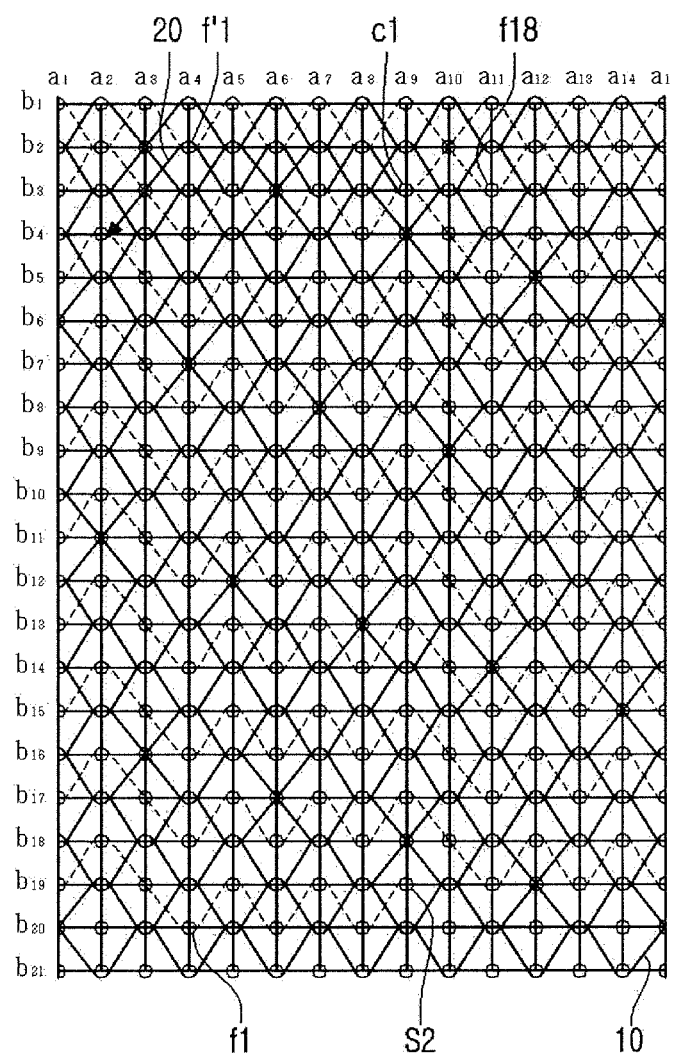
FIGS. 12 and 13 are developments illustrating a second wire lowering step according to the present invention.
Figure 13:
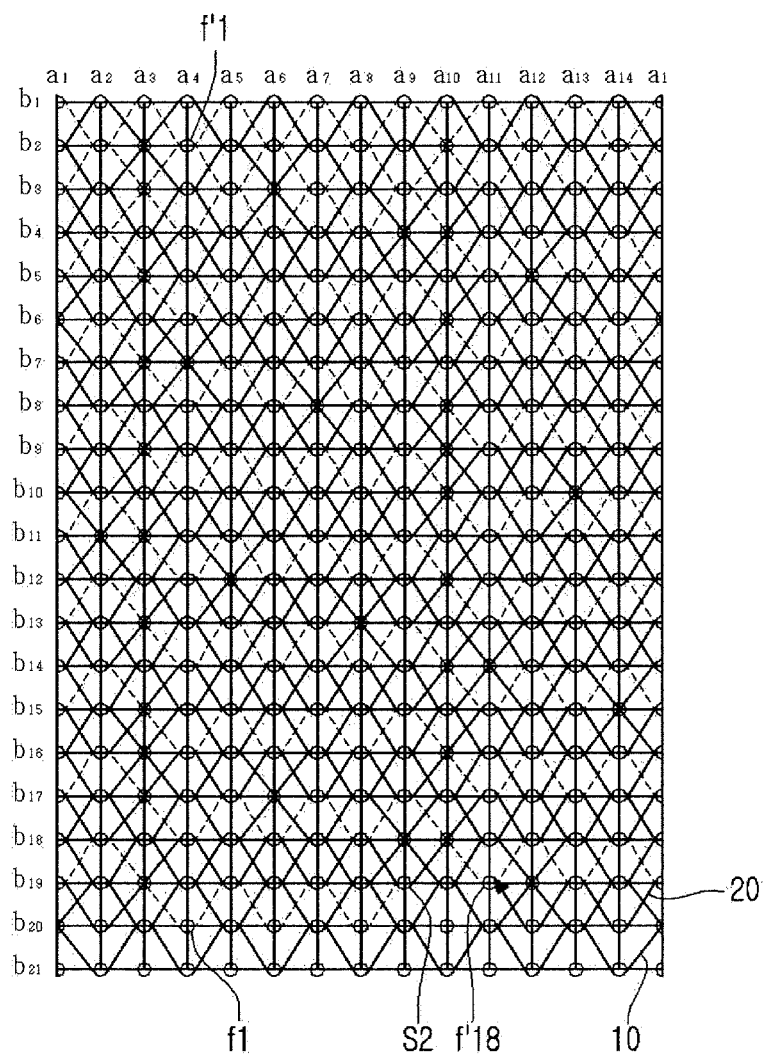

As shown in FIGS. 12 and 13, at the present step (step G), the second wire 20 is bent and moved in a zigzag form from the second change point c1 at the one end of the jig to a fourth point F'18 ($a_{11}/b_{19}$) at the other end of the jig.

As shown in FIG. 12, this process includes: a third zigzag movement step (step G-1) of repeating a zigzag bent pattern formed by moving the second wire 20 from the second change point c1 along an upward diagonal line by l (the distance of a diagonal line extending by one interval between the length division lines with respect to one interval between the circumference division lines) and then moving the second wire 20 from a corresponding location point $a_8/b_2$ along a downward diagonal line by t; and a fourth spacing step (step G-2) of spacing a corresponding location point from a portion formed at the zigzag movement step by moving the second wire 20 from the end point F'1 ($a_d/b_2$) of the third zigzag movement step along a downward diagonal line by 2l.

The patterns of the third zigzag movement step and the fourth spacing step are alternately performed, and the third zigzag movement step to be performed after the first fourth spacing step starts from a location point $a_2/b_4$ reached by spacing the second wire 20 via the previously performed fourth spacing step. As shown in FIG. 13, the patterns of the two steps are repeated, and then the second wire lowering step S700 is terminated at the end point F'18 of a specific third zigzag movement step.

As a result, a fourth point, which is the last location of the second wire lowering step S700 and which is also the start location of a lower second head formation step S800, corresponds to the last end point F'18 of a plurality of end points F'1, F'2, F'3, . . . , F'18 formed during the process in which the third zigzag movement step and the fourth spacing step are alternately performed. This fourth point F'15 refers to an end point which is one of the plurality of end points F'1, F'2, F'3, . . . , F'18 formed during the process in which the third zigzag movement step and the fourth spacing step are alternately performed and which is located on the same length division line as the second start point S2.

(8) Lower Second Head Formation Step <S800>

Figure 14:
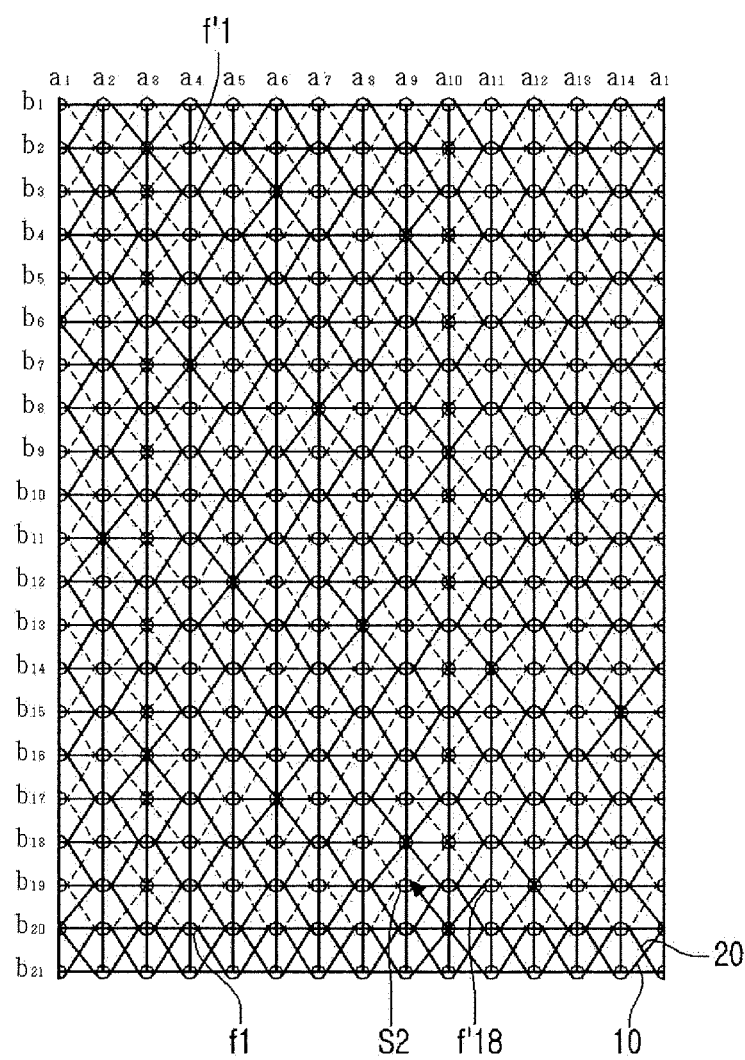
FIG. 14 is a development illustrating an upper second head formation step according to the present invention.

As shown in FIG. 14, at the present step (step H), there is performed a process of forming a lower second head by repeating a pattern of bending the second wire 20 in a zigzag form the fourth point F'18, reached after the second wire 20 has formed the intersection structure of the second wire 20 forming the part of the second body of the stent while being lowered via step S700 (step G), thus resulting in the completion of the intersection structures of the wires 10 and 20 of the overall body, to the second start point S2 at the other end of the jig, thus resulting in the completion of the intersection structures of the wires 10 and 20 of the overall lower head.

In this case, the second wire 20 is moved from the fourth point F'18 along an downward diagonal line by 2l, as shown in FIG. 14 (step H-1).

Thereafter, a bent pattern formed by moving the second wire 20 from a corresponding location point $a_9/b_{21}$ along an upward diagonal line by l and then moving the second wire 20 from a corresponding location point $a_8/b_{20}$ along a downward diagonal line by l is repeated until the second wire 20 is located on the same circumference division line $a_{11}$ as the fourth point F'18 (step H-2).

Finally, the second wire 20 is located at the second start point S2 by moving the second wire 20 from a location point $a_{11}/b_{21}$, reached as a result of the above step, along an upward diagonal line by 2l (step H-3).

Figure 15:
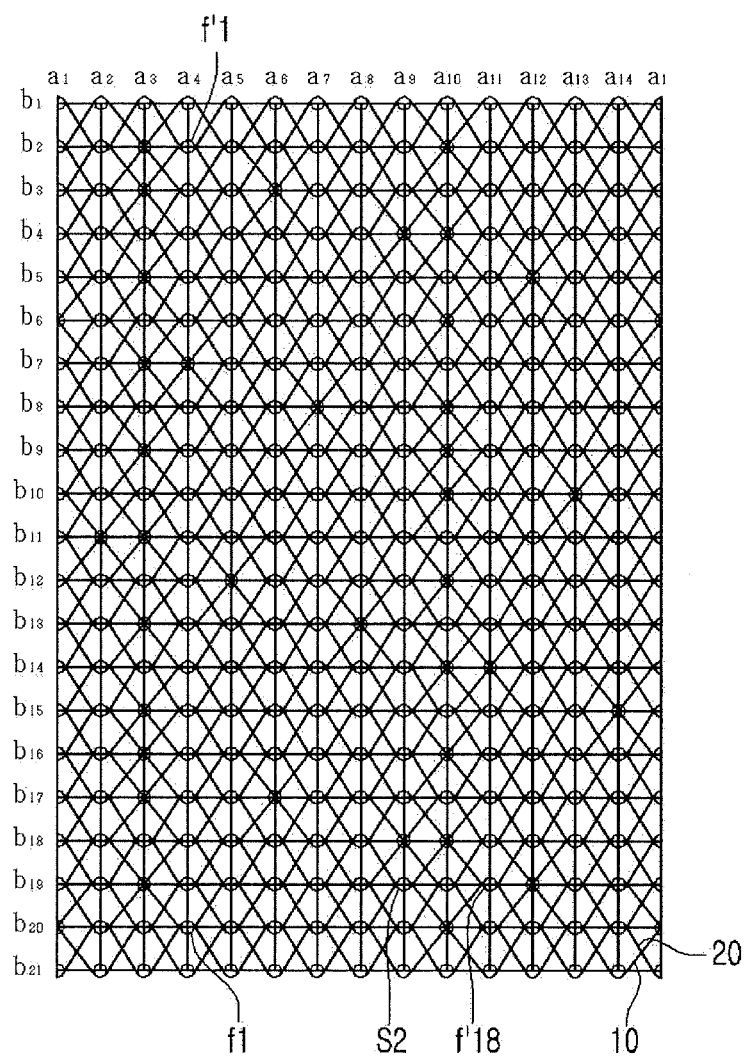
FIGS. 15 and 16 are developments showing the overall intersection and bending state of first and second wires according to the present invention.

As shown in FIG. 15, the second wire 20 returned to the second start point S2 as described above is finally connected through welding or the like, and forms the second stent having predetermined structural characteristics. Furthermore, as shown in FIG. 16, the inner first stent structure completed by using the first wire 10 and the outer second stent structure completed by using the second wire 20 may be connected and provided as a single stent.

2. <Description of Characteristics of the Stent Manufactured by the Method for Manufacturing a Stent According the Present Invention>

First, in the case of the first stent manufactured via steps S100 to S400 of the method for manufacturing a stent according to the present invention, the intersection portions B1 to B19 are formed in a diagonal direction in a spiral form one for each length division line, and ring-shaped portions A are formed in the remaining portions, as shown in FIGS. 7 and 8.

In this case, as shown in FIG. 8, two wire sections are connected to each other in the form of being hooked around each other at two intersection points in each of the remaining portions excluding the intersection portions B1 to B19 formed one for each length division line, and the ring-shaped portions A in each of which an empty circular space is provided by protruding pins P are formed in the centers of the remaining portions. When the overall structure of the stent is changed, these ring-shaped portions A not only prepare sufficient spaces for changes in the shapes of cells, but also provide spaces in which intersection wire structure can be deformed and located so that the overall structure of the stent can be easily bent, thereby enabling the first stent to have high-level structural flexibility.

Furthermore, on the respective length division lines, the plurality of intersection portions B2, B3, B4, . . . , B19 are sequentially formed from the intersection portion B1, formed at the specific location point $a_3/b_2$ on the second length division line $b_2$, along a diagonal line having a predetermined slope at regular intervals one for each length division line. These intersection portions B1 to B19 provide resisting force-type stress adapted to maintain the structure and location of the stent against forces applied in a direction toward the center of the stent after the placement of the stent, including external force applied to both side ends of the stent due to movement continuously occurring in a stenosed region of a patient after the placement of the stent in the stenosed region.

However, in the case of the conventional stent, structures based on a predetermined intersection method are regularly formed in the lengthwise direction of the stent. In particular, the stent is formed in a manner in which intersection portions are provided on a specific circumference division line in the lengthwise direction of the stent. Accordingly, the resisting force-type stress generated in the intersection portions is cancelled out by force generated in the portions formed based on an intersection method, different from the intersection method of the intersection portions, on the circumference division lines on both sides of the circumference division line where the intersection portion are formed. As a result, sufficient stress cannot be provided against external force applied to the stent, and thus the conventional stent is problematic in that a wire structure is bent or the stent is dislodged from a stenosed region where the stent has been placed.

In contrast, in the first stent manufactured via steps S100 to S400 of the method for manufacturing a stent according to the present invention, the intersection portions B1 to B19 are spaced apart from each other in a diagonal direction one for each length division line and form a spiral arrangement structure. Accordingly, the first stent has not only structural flexibility but also resisting force sufficient to maintain the structure and location of the stent against external force applied to both ends of the stent.

Furthermore, in the case of the second stent additionally manufactured via steps S500 to S800 of the method for manufacturing a stent according to the present invention on the jig used for manufacture after the first stent has been manufactured, the intersection method for wire sections located on the specific circumference division lines $a_3$ and $a_{10}$ forms the intersection portions B in each of which one wire section simply passes over another wire section, and the intersection method for wire sections on the remaining circumference division lines forms ring-shaped portions A in each of which wire sections surround both sides of a corresponding protruding pin P and a circular space portion is provided, as shown in FIGS. 15 and 16.

In this case, when a hollow cylindrical stent is implemented by connecting the circumference division lines a1 at both side ends of the development shown in FIG. 15, the second stent is formed such that only wire intersection structures on two opposite pairs of circumference division lines $a_3$ and $a_{10}$ form intersection portions B and wire intersection structures on the remaining circumference division lines form ring-shaped portions A, thereby providing having high-level flexibility which can easily cause structural changes.

In the second stent, the part of the second body is formed such that the second wire 20 is located over the first wire 10 at one intersection point (an intersection point formed in a space between $a_3$ and $a_4$ and between $b_{19}$ and $b_{20}$) of the two intersection points formed during the process of moving the second wire 20 from each of the end points of the second zigzag movement step along an upward diagonal line via the third spacing step of the second wire raising step S500

(which is indicated by a small circle in FIG. 10; X1), and such that the second wire 20 is located beneath the first wire 10 at the other point (an intersection point formed in a space between $a_2$ and $a_3$ and between $b_{18}$ and $b_{19}$) (which is indicated by a small triangle in FIG. 10; X2). Accordingly, the second stent is coupled to the first stent in the space between $a_2$ and $a_3$ and between $b_{18}$ and $b_{19}$, and thus reinforces the structural characteristics of the first stent.

In other words, the second stent is coupled to the first stent in the space between $a_2$ and $a_3$ and between $b_{18}$ and $b_{19}$ to form a restraining structure in the lengthwise direction, thereby preventing the first stent from being twisted and also providing more improved structural flexibility to the overall stent structure.

In other words, the stent completed via the manufacturing method according to the present invention is located suitable for the shape of a lumen, in which a stenosis has occurred, based on high-level flexibility, and has axial force close to 0 acting in the axial direction of the stent and high-level radial force inflating the stent to the outside. Accordingly, outstanding durability based on low wire fatigue can be provided. Furthermore, the stent provides sufficient resisting force against external force applied from both ends of the stent in a direction toward the center of the stent due to movement occurring in a region where the stent has been placed after the placement of the stent, thereby preventing the stent from being bent and dislodged.

As a result, the present invention takes into account a demand for a method for manufacturing a stent which can maintain the structural flexibility of a recent stent requiring improvements in durability and service life as the average life span of cancer patients increases and which can also provide a sufficient service life.

The embodiments disclosed in the present invention are not intended to limit the technical spirit of the present invention, but are intended to illustrate the technical spirit of the present invention. The scope of the technical spirit of the present invention is not limited by these embodiments. The range of protection should be interpreted based on the attached claims, and all technical spirits falling within the equivalent range of the claims should be interpreted as being included in the range of rights of the present invention.

DESCRIPTION OF REFERENCE SYMBOLS

10: first wire
20: second wire
P: protruding pin
A: ring-shaped portion
B: intersection portion

The invention claimed is:

1. A method for manufacturing a stent, the method using a jig in which detachable protruding pins are installed at all respective location points at which circumference division lines and length division lines, set by equally dividing a circumference (W) and length (L) of a cylinder having a diameter (R) and the length (L) identical to those of a stent to be manufactured, intersect each other, the method forming cells through intersection of a wire by setting any one reference point of the location points as a start point and repeatedly bending and moving the wire from the start point upward and downward to pass over the protruding pins located in diagonal directions, the method comprising:
step A of forming part of a first body by moving a first wire in a zigzag form from a first start point at one end of the jig to a first point at the other end of the jig;
step B of forming a lower first head by repeating a pattern of bending the first wire in a zigzag form from the first point to a first change point at the other end of the jig;
step C of forming part of the first body by bending and moving the first wire in a zigzag form from the first change point to a second point at the one end of the jig; and
step D of forming an upper first head by repeating a pattern of bending the first wire in a zigzag form from the second point to the first start point;
wherein step A comprises:
step A-1 of moving the first wire from the first start point along an upward diagonal line by l, wherein l is a distance of a diagonal line extending by one interval between the length division lines with respect to one interval between the circumference division lines; and
step A-2 of spacing a corresponding location point from a portion formed at step A-1 by moving the first wire from an end point of step A-1 along a downward diagonal line by 2l;
wherein step C comprises:
step C-1 of repeating a zigzag bent pattern formed by moving the first wire from the first change point along a downward diagonal line by l and then moving the first wire from a corresponding location point along an upward diagonal line by l; and
step C-2 of spacing a corresponding location point from a portion formed at step C-1 by moving the first wire from an end point of step C-1 along an upward diagonal line by 2l;
wherein step A comprises alternately repeating patterns of step A-1 and step A-2; and
wherein step C comprises alternately repeating patterns of step C-1 and step C-2.

2. The method of claim 1, wherein a number of circumference division lines is 6+4x, wherein x is 0 or a natural number, and a number of length division lines is 11+5y, wherein y is 0 or a natural number.

3. The method of claim 2, wherein:
the first point corresponds to an end point which is one of a plurality of end points of step A-1 formed during the repetition of step A-1 and step A-2 and which is also located on a length division line symmetrical to a length division line where the first start point is located; and
the second point corresponds to an end point which is one of a plurality of end points of step C-1 formed during the repetition of step C-1 and step C-2 and which is also located on a same length division line as the first start point.

4. The method of claim 3, wherein:
step B comprises:
step B-1 of moving the first wire from the first point along a downward diagonal line by 2l;
step B-2 of repeating a zigzag bent pattern formed by moving the first wire from a location point, reached at step B-1, along an upward diagonal line by l and then moving the first wire from a corresponding location point along a downward diagonal line by l; and
step B-3 of locating the first wire at the first change point by moving the first wire from a location point, reached at step B-2, along an upward diagonal line by 2l; and
the location point reached at step B-2 is located on a same circumference division line as the first point.

5. The method of claim 3, wherein:
step D comprises:
step D-1 of moving the first wire from the second point along an upward diagonal line by 2l;
step D-2 of repeating a zigzag bent pattern formed by moving the first wire from a location point, reached at step D-1, along a downward diagonal line by l and then moving the first wire from a corresponding location point along an upward diagonal line by l; and
step D-3 of locating the first wire at the first start point by moving the first wire from a location point, reached at step D-2, along a downward diagonal line by 2l; and
the location point reached at step D-2 is located on a same circumference division line as the second point.

6. The method of claim 1, further comprising:
step E of forming part of a second body by bending and moving a second wire in a zigzag form from a second start point at the other end of the jig to a third point at the one end of the jig;
step F of forming an upper second head by repeating a pattern of bending the second wire in a zigzag form from the third point to a second change point at the one end of the jig;
step G of forming part of the second body by bending and moving the second wire in a zigzag form from the second change point to a fourth point at the other end of the jig; and
step H of forming a lower second head by repeating a pattern of bending the second wire in a zigzag form from the fourth point to the second start point;
wherein step E comprises:
step E-1 of repeating a zigzag bent pattern formed by moving the second wire from the second start point along a downward diagonal line by l and then moving the second wire from a corresponding location point along an upward diagonal line by l; and
step E-2 of spacing a corresponding location point from a portion formed at step E-1 by moving the second wire from an end point of step E-1 along an upward diagonal line by 2l;
wherein step G comprises:
step G-1 of repeating a zigzag bent pattern formed by moving the second wire from the second change point along an upward diagonal line by l and then moving the second wire from a corresponding location point along a downward diagonal line by l; and
step G-2 of spacing a corresponding location point from a portion formed at step G-1 by moving the second wire from an end point of step G-1 along a downward diagonal line by 2l;
wherein step E comprises alternately repeating patterns of step E-1 and step E-2;
wherein step G comprises alternately repeating patterns of step G-1 and step G-2; and
wherein step E-2 comprises moving the second wire so that during the movement of the second wire, the second wire is located over the first wire at one of two points at which the first wire and the second wire woven on the jig intersect each other and the second wire is located beneath the first wire at a remaining point of the two points.

7. The method of claim 6, wherein the second start point corresponds to a location which is reached by moving a corresponding circumference division line by an odd number of intervals in a circumferential direction along a length division line symmetrical to a length division line where the first start point is located.

8. The method of claim 7, wherein:
the third point corresponds to an end point which is one of a plurality of end points of step E-1 formed during the repetition of step E-1 and step E-2 and which is also located on a length division line symmetrical to a length division line where the second start point is located; and
the fourth point corresponds to an end point which is one of a plurality of end points of step G-1 formed during the repetition of step G-1 and step G-2 and which is also located on a same length division line as the second start point.

9. The method of claim 6, wherein:
step F comprises:
step F-1 of moving the second wire from the third point along an upward diagonal line by 2l;
step F-2 of repeating a zigzag bent pattern formed by moving the second wire from a location point, reached at step B-1, along a downward diagonal line by l and then moving the second wire from a corresponding location point along an upward diagonal line by l; and
step F-3 of locating the second wire at the second change point by moving the second wire from a location point, reached at step F-2, along a downward diagonal line by 2l;
wherein the location point reached at step F-2 is located on a same circumference division line as the third point.

10. The method of claim 6, wherein:
step H comprises:
step H-1 of moving the second wire from the fourth point along a downward diagonal line by 2l;
step H-2 of repeating a zigzag bent pattern formed by moving the second wire from a location point, reached at step H-1, along an upward diagonal line by l and then moving the second wire from a corresponding location point along a downward diagonal line by l; and
step H-3 of locating the second wire at the second start point by moving the second wire from a location point, reached at step H-2, along an upward diagonal line by 2l; and
the location point reached at step H-2 is located on a same circumference division line as the fourth point.

* * * * *